United States Patent [19]

Shima et al.

[11] Patent Number: 6,004,949

[45] Date of Patent: Dec. 21, 1999

[54] AQUEOUS COMPOSITION CONTAINING CROMOGLYCIC ACID

[75] Inventors: Junko Shima; Kazuhiro Ono; Takashi Osada; Yukio Suzuki, all of Tokyo, Japan

[73] Assignee: Showa Yakuhin Kako Co., Ltd., Tokyo, Japan

[21] Appl. No.: 09/091,891

[22] PCT Filed: Dec. 27, 1995

[86] PCT No.: PCT/JP95/02724

§ 371 Date: Jun. 26, 1998

§ 102(e) Date: Jun. 26, 1998

[87] PCT Pub. No.: WO97/24142

PCT Pub. Date: Jul. 10, 1997

[51] Int. Cl.[6] .......................... A61K 31/33; A61K 31/355
[52] U.S. Cl. ............................................ 514/183; 514/458
[58] Field of Search ...................................... 514/183, 458

[56] References Cited

FOREIGN PATENT DOCUMENTS

| 54-25082 | 8/1979 | Japan . |
|---|---|---|
| 62-292719 | 12/1987 | Japan . |
| 4-66452 | 10/1992 | Japan . |
| 4-78613 | 12/1992 | Japan . |
| 6-74212 | 9/1994 | Japan . |
| 1399834 | 7/1975 | United Kingdom . |

*Primary Examiner*—Zohreh Fay
*Attorney, Agent, or Firm*—Birch, Stewart, Kolasch & Birch, LLP

[57] ABSTRACT

An aqueous pharmaceutical composition comprising sodium cromoglicate as an active ingredient and a quaternary ammonium compound such as benzalkonium chloride as a preservative, characterized in that said composition comprises a precipitation inhibitor selected from the group consisting of alkanolamines including 2-aminoethanol and tocopherols including d-α-tocopherol is provided. The composition has characteristic feature of free from precipitation or turbidity in manufacturing processes and during storage.

10 Claims, No Drawings

AQUEOUS COMPOSITION CONTAINING CROMOGLYCIC ACID

This application claims the benefit under 35 U.S.C. §371 of prior PCT International Application No. PCT/JP95/02724 which has an International filing date of Dec. 27, 1995 which designated the United States of America, the entire contents of which are hereby incorporated by reference.

TECHNICAL FIELD

The present invention relates to an aqueous pharmaceutical composition which comprises sodium cromoglicate, an antiallergic agent, as an active ingredient and is useful as an eye drop, an injections and the like.

BACKGROUND ART

Aqueous pharmaceutical compositions in the form of eye drops, nasal drops or other, which comprise sodium cromoglicate [disodium salt of 1,3-bis(2-carboxychromon-5-yloxy)-2-hydroxypropane] having antiallergic activity as an active ingredient, have been used for preventive and therapeutic treatment of allergic conjunctivitis and allergic rhinitis.

It has been known that turbidity or precipitation tends to quite frequently appear in an aqueous pharmaceutical compositions comprising sodium cromoglicate as an active ingredient (see, for example, Japanese Patent Publication (KOKOKU) Nos. (Hei)4-66452/1992 and (Hei)4-78613/1992). It is recognized that the turbidity or precipitation is formed because a quaternary ammonium compound such as benzalkonium chloride, which is added as a preservative, reacts with sodium cromoglicate in the presence of trace metal ions ($Pb^{2+}$, $Ca^{2+}$, $Cu^{2+}$, $Al^{2+}$, $Fe^{2+}$, $Fe^{3+}$, $Zn^{2+}$, $Mg^{2+}$ or other) contained in the aqueous solution. Recent researches by the inventors of the present invention revealed that the reaction of benzalkonium chloride and sodium cromoglicate as well as resulting precipitation of reaction products are remarkably accelerated especially when concentrations of calcium ion and magnesium ion in the aqueous solution exceed 1 ppm and 10 ppm, respectively.

The generation of turbidity or precipitation seriously disturbs a process of manufacturing an aqueous pharmaceutical composition comprising sodium cromoglicate as an active ingredient, and this is also a significant problem from a viewpoint of storage stability of pharmaceutical preparations. However, considerable amounts of magnesium and calcium are contained as unavoidable impurities in bulk powder of sodium cromoglicate used as a raw material of pharmaceutical preparations, and distilled water for injection used as a solvent also contains a trace amount of metal ions. Therefore, it is practically impossible to achieve complete prevention of the generation of turbidity or precipitation by improving quality of raw materials and circumstantial conditions of a manufacturing process.

For the manufacture of an aqueous composition comprising sodium cromoglicate, methods of adding a precipitation inhibitor (sequestering agent) such as a chelating agent or a nonionic surfactant to the aqueous composition have thus been proposed as means to effectively prevent the generation of turbidity and precipitation.

For example, the following means have been proposed: an aqueous composition comprising sodium cromoglicate as an active ingredient that is added with an effective amount of a pharmaceutically acceptable chelating agent or sequestering agent when a concentration of a metal ion in the aqueous solution exceeds 0.40 ppm (Japanese Patent Publication (KOKOKU) No. (Sho)54-25082/1979); a water-soluble pharmaceutical preparation added with benzalkonium chloride as a preservative and polyoxyethylene sorbitan monooleate or polyoxyethylene hardened castor oil as an agent for preventing turbidity or precipitation (Japanese Patent Publication (KOKOKU) No. (Hei)4-66452/1992); and an external pharmaceutical preparation containing benzalkonium chloride as a preservative and a nonionic surfactant such as polyoxyethylene hardened castor oil in respective particular amounts (Japanese Patent Publication (KOKOKU) No. (Hei)4-78613/1992).

DISCLOSURE OF THE INVENTION

An object of the present invention is to provide an aqueous pharmaceutical composition comprising sodium cromoglicate as an active ingredient and useful as an eye drop or an injection, which is stable and free from generation of turbidity or precipitation during manufacturing processes, storage and distribution.

The inventors of the present invention conducted various studies to achieve the foregoing object, and as a result, they found that the generation of turbidity or precipitation is remarkably suppressed by adding 2-aminoethanol or a tocopherol to an aqueous solution containing sodium cromoglicate as an active ingredient and benzalkonium chloride as a preservative. The inventors of the present invention conducted further researches based on the above findings, and achieved the present invention.

The present invention thus provides an aqueous pharmaceutical composition comprising sodium cromoglicate as an active ingredient and a quaternary ammonium compound as a preservative, characterized in that said composition further comprises a precipitation inhibitor selected from the group consisting of alkanolamines and tocopherols. According to another embodiment of the present invention, there are provided a precipitation inhibitors selected from the group consisting of an alkanolamine and a tocopherol for a formulation of an aqueous pharmaceutical composition comprising sodium cromoglicate as an active ingredient and a quaternary ammonium compound as a preservative,.

BEST MODE FOR CARRYING OUT THE INVENTION

Sodium cromoglicate [chemical name: 1,3-bis(2-carboxychromon-5-yloxy)-2-hydroxypropane disodium salt or disodium-5,5'-[(2-hydroxytrimethylene)dioxy]bis[4oxo-4H-1-benzopyran-2-carboxylate] contained in the aqueous composition of the present invention is widely used as an active ingredient of, for example, nasal drops and eye drops for nasal and ophthalmic allergic diseases. For example, a concentration of the ingredient may generally be about 1.5 to 4.0% by weight when used as external aqueous compositions such as nasal drops and eye drops.

As the quaternary ammonium compound formulated as a preservative, benzalkonium chloride, benzethonium chloride and other may be used. Among them, it is preferred to use benzalkonium chloride from a viewpoint of antibacterial activity. Benzalkonium chloride is represented by the general formula $[C_6H_5CH_2N(CH_2R]^+Cl^-$, wherein an alkyl group represented by R has about 8 to 18 carbon atoms. This compound is generally provided as a mixture of the plural compounds having a $C_8$–$C_{18}$ alkyl group, however, the compound having a specific alkyl group or a particular mixture composed of the compounds having specific alkyl groups may also be used. For example, since it is known that a mixture of the compounds having $C_{13}$- or lower alkyl groups, and the compound having $C_{12}$-alkyl group are preferred from a viewpoint of suppression of precipitation or turbidity (Japanese Patent Publication [KOKOKU] No. (Hei)6-74212/1994), such substances may be used according to preferred embodiments of the present invention. A concentration of the preservative is not particularly limited so far that the concentration is within a range generally applied to aqueous pharmaceutical compositions. For example, a concentration of about 0.001 to 0.05% by weight is preferred.

The composition of the present invention is characterized in that one or more substances selected from the group consisting of an alkanolamine and a tocopherol as a precipitation inhibitor is formulated in an aqueous composition which comprises the aforementioned sodium cromoglicate and a quaternary ammonium compound as a preservative. The term "precipitation inhibitor" herein used should be understood to embrace any agents that have reducing or suppressing actions on, for example, the increase of turbidity which is visibly and/or spectrophotometrically observable, as well as on the generation of precipitation including visible white turbidity. The terms "precipitation or turbidity" should be construed to have the broadest meanings including those generated during a mixing process of the ingredients and subsequent production processes, and those generated during storage and distribution of final products. Although it is not intended to be bound by any specific theory, such precipitation or turbidity is formed by reaction of the quaternary ammonium compound with sodium cromoglicate in the presence of a trace amount of metal ions contained in the aqueous solution.

The alkanolamines have a structure that is composed of a linear or branched alkane having 2 to 12 carbon atoms substituted with one or more hydroxyl groups and one or more amino groups at arbitrary positions. Preferably, those composed of a linear or branched alkane having 2 to 6 carbon atoms that is substituted with one hydroxyl group and one amino group may be used. For example, 2-aminoethanol (ethanolamine), 1-amino-2-propanol 2-aminopropanol (alaninol), 3-aminopropanol, 2-aminobutanol, 2-aminohexanol, 6-aminohexanol, mixtures thereof or other may be used. Among them, 2-aminoethanol may preferably be used.

As the alkanolamine, optically active substances and diastereoisomers in pure forms, any mixtures thereof, racemates and the like may be used. Alkanolamines in the form of pharmaceutically acceptable acid addition salts may also be used. For example, mineral acid salts such as hydrochloride, sulfate, nitrate, and phosphate, or organic acid salts such as citrate, malate, oxalate, tartrate, and methanesulfonate may be used.

As the tocopherol, α, β, γ and δ-tocopherols and any mixtures thereof may be used. Tocopherols are generally added to foods or drugs as an antioxidant. It is known that tocopherol derivatives are available which are almost equivalent to tocopherol from a viewpoint of anti-oxidizing activity. Examples of such derivatives include α-tocopheryl acetate, α-tocopheryl succinate and the like, and these derivatives may also be used as the precipitation inhibitor. It is also known that optically active isomers exist for each of the aforementioned tocopherol isomers and the tocopherol derivatives, and any one of naturally occurring d-isomers and chemically synthesized dl-compounds may be added in the composition of the present invention. Among them, it is preferred to use d-α-tocopherol or dl-α-tocopherol and d-α-tocopherol is most preferably used.

A formulation amount of the precipitation inhibitor in the composition of the present invention is not particularly limited, and the amount may be suitably chosen depending on a formulation amount of sodium cromoglicate as an active ingredient, a type and amount of the quaternary ammonium compound as a preservative, and amounts of trace metal ions such as magnesium and calcium ions in the aqueous composition. For example, the precipitation inhibitor may be added in an amount of 0.01 to 5.0% by weight, preferably 0.1 to 1.0% by weight.

The composition of the present invention may be added with pharmaceutical additives ordinarily used for the manufacture of external aqueous compositions such as eye drops and aqueous compositions such as injections. Examples of such additives include, for example, buffering agents such as dibasic sodium phosphate and boric acid; isotonic agents such as sodium chloride and glycerin; stabilizers such as disodium edetate; and pH modifiers such as hydrochloric acid or sodium hydroxide. It is known that addition of a nonionic surfactant such as polyoxyethylene sorbitan monooleate and polyoxyethylene hardened castor oil to an aqueous composition comprising sodium cromoglicate and a quaternary ammonium compound suppresses the formation of precipitation or turbidity (Japanese Patent Publication (KOKOKU) Nos. (Hei)4-66452/1992 and (Hei)4-78613/1992), and therefore, a nonionic surfactant may be added to the composition of the present invention.

Methods for manufacturing the composition of the present invention are not particularly limited. For example, the composition can be prepared by dissolving necessary amounts of the aforementioned ingredients in distilled water for injection successively or at one time, optionally adjusting pH to a suitable range, and then sterilizing the solution by means of a membrane filter or the like. The formation of precipitation may sometimes be accelerated where a large amount of metal ions such as $Mg^{2+}$ or $Ca^{2+}$ are contained in raw materials for the formulation, e.g., sodium cromoglicate, the quaternary ammonium compound, additives for pharmaceutical preparations such as buffering agents, and/or solvents such as sterilized distilled water and distilled water for injection. Therefore, as the raw materials for the formulation, those with an adequate purity, as high as possible, should be used. In particular, it is preferred to use the raw materials for the formulation which contain least amounts of metal ions such as $Mg^{2+}$ or $Ca^{2+}$.

The composition of the present invention may be used as external pharmaceutical formulations such as eye drops and nasal drops, or pharmaceutical preparations for parenteral administration such as inhalants, injections and drip infusions. Among them, eye drops and nasal drops are preferred embodiments of the composition of the present invention.

EXAMPLES

Example 1: Formulation Examples

Examples of compositions that are suitably used as eye drops, nasal drops or other will be explained. However, the compositions of the present invention are not limited to these examples (percentages described in the formulations are in percent by weight). Any of these formulations may optionally be adjusted to pH 6.0 by using an appropriate amount of diluted hydrochloric acid or sodium hydroxide.

Formulation Example 1

| | |
|---|---|
| Sodium cromoglicate | 2% |
| Benzalkonium chloride | 0.01% |

-continued

| | |
|---|---|
| 2-Aminoethanol | 1% |
| Distilled water for injection | Appropriate amount |

Formulation Example 2

| | |
|---|---|
| Sodium cromoglicate | 2% |
| Benzalkonium chloride | 0.01% |
| d-α-Tocopherol | 0.1% |
| Distilled water for injection | Appropriate amount |

Formulation Example 3

| | |
|---|---|
| Sodium cromoglicate | 2% |
| Benzalkonium chloride (R = $C_{12}$) | 0.01% |
| 2-Aminoethanol | 0.1% |
| Sodium chloride | 0.4% |
| Distilled water for injection | Appropriate amount |

Formulation Example 4

| | |
|---|---|
| Sodium cromoglicate | 2% |
| Benzalkonium chloride | 0.01% |
| 2-Aminoethanol | 1% |
| Sodium edetate | 0.01% |
| Distilled water for injection | Appropriate amount |

Example 2: Preparation Example

Sodium cromoglicate (10 g), benzalkonium chloride (0.05 g), and 2-aminoethanol (ethanolamine, 5 ml) were added to distilled water for injection and dissolved. The solution was adjusted to pH 6.0 by addition of an appropriate amount of diluted hydrochloric acid, and then added with distilled water for injection up to a total volume of 500 ml. The resulting solution was filtered by using a membrane filter (pore size: 0.22 μm) to obtain a composition of the present invention.

Example 3: Test Examples

Previous researches conducted by the inventors of the present invention revealed that the reaction of benzalkonium chloride and sodium cromoglicate is markedly accelerated when a concentration of magnesium ion in an aqueous solution is not lower than 1 ppm. On the basis of the findings, a composition as a positive control was prepared by adding 8 ppm of $MgCl_2$ (8 mg of $MgCl_2$ per 1,000 ml of an aqueous composition) as a source of magnesium ions to an aqueous composition comprising benzalkonium chloride (0.01%) and sodium cromoglicate (2%). Compositions were prepared by adding a test compound to the control composition, and appearances of the positive control composition and the test composition were compared after storage for a given period of time to evaluate suppressing effect of the test compound on precipitation.

(A) Preparation of the Positive Control Composition

Magnesium chloride (4 mg) was dissolved in about 400 ml of distilled water for injection, and then sodium cromoglicate (10 g) and benzalkonium chloride (0.05 g) were added to the resulting solution and dissolved. The solution was adjusted to pH 6.0 by adding an appropriate amount of diluted hydrochloric acid, and then added with distilled water for injection up to a total volume of 500 ml. The solution was filtered by using a membrane filter (pore size: 0.22 μm) to obtain the positive control composition.

(B) Preparation of the Test Composition

Magnesium chloride (4 mg) was dissolved in about 400 ml of distilled water for injection, and then sodium cromoglicate (10 g), benzalkonium chloride (0.05 g) and a test compound (5 g, or 5 ml for liquid) were added to the resulting solution and dissolved. The solution was adjusted to pH 6.0 by adding an appropriate amount of diluted hydrochloric acid or diluted sodium hydroxide, and then added with distilled water for injection up to a total volume of 500 ml. The solution was filtered by using the same membrane filter as above to obtain a test composition.

(C) Test Method and Results

The positive control composition and the test compositions were stored for two days at 5° C., and formation of visible precipitation or turbidity was evaluated. The results are shown in the table below. The evaluation criteria for the test compositions are as follows: ⊚: no precipitation or turbidity is observed; ○: slight white turbidity is observed; and ×: precipitation or turbidity is clearly observed. From these results, it can be clearly understood that precipitation inhibitors selected from the group consisting of alkanolamines and tocopherols remarkably suppress the formation of precipitation or turbidity in an aqueous composition comprising sodium cromoglicate and benzalkonium chloride.

| Composition No. | Test compound | Evaluation | Appearance after storage |
|---|---|---|---|
| Positive control | No addition | × | Formation of white precipitation |
| 1 (Inventive) | 2-Aminoethanol | ⊚ | Pale yellow, transparent |
| 2 (Inventive) | 3-Aminopropanol | ⊚ | " |
| 3 (Inventive) | 6-Aminohexanol | ⊚ | " |
| 4 (Inventive) | d-α-Tocopherol | ⊚ | " |
| 5 (Comparative) | Tween 80* | ○ | Slight white turbidity |
| 6 (Comparative) | n-Octylamine | ○ | " |
| 7 (Comparative) | L-Glutamic acid | ○ | " |
| 8 (Comparative) | L-Asparagine | ○ | " |
| 9 (Comparative) | Ethanol | × | Formation of white precipitation |
| 10 (Comparative) | Butanol | × | Formation of white precipitation |
| 11 (Comparative) | Ammonia | × | Solidified, gel |
| 12 (Comparative) | p-Aminophenol | × | Formation of black precipitation |

*Polyoxyethylene (20) sorbitan monooleate

INDUSTRIAL APPLICABILITY

The compositions of the present invention can be used as aqueous pharmaceutical compositions such as eye drops and nasal drops for preventive and therapeutic treatment of allergic diseases. The compositions can achieve stable supply of the medicament as one of characteristic features since they are free from precipitation or turbidity during manufacturing process and storage.

What is claimed is:

1. An aqueous pharmaceutical composition comprising sodium cromoglicate as an active ingredient and a quaternary ammonium compound as a preservative, characterized in that said composition comprises a precipitation inhibitor selected from the group consisting of alkanolamines and tocopherols.

2. The composition according to claim 1 wherein the preservative is benzalkonium chloride.

3. The composition according to claim 1 or 2 wherein the precipitation inhibitor is 2-aminoethanol.

4. The composition according to claim 1 or 2 wherein the precipitation inhibitor is d-α-tocopherol or dl-α-tocopherol.

5. A precipitation inhibitor for a formulation of an aqueous pharmaceutical composition comprising sodium cromoglicate as an active ingredient and a quaternary ammonium compound as a preservative, which is selected from the group consisting of alkanolamines and tocopherols.

6. The precipitation inhibitor according to claim 5 which is selected from the group consisting of 2-aminoethanol, d-α-tocopherol, and dl-α-tocopherol.

7. An aqueous pharmaceutical composition comprising sodium cromoglicate as an active ingredient, a benzalkonium chloride as a preservative, and a precipitation inhibitor selected from the group consisting of 2-aminoethanol and d-α-tocopherol or dl-α-tocopherol.

8. The composition according to claim 1, wherein the active ingredient is present in an amount of about 1.5 to 4.0% by weight.

9. The composition of claim 1, wherein the preservative is present in a concentration of about 0.001 to 0.05% by weight.

10. The composition according to claim 1, wherein the precipitation inhibitor is present in an amount of 0.01 to 5.0% by weight.

* * * * *